US007790453B2

(12) United States Patent
Caplice

(10) Patent No.: US 7,790,453 B2
(45) Date of Patent: Sep. 7, 2010

(54) SMOOTH MUSCLE PROGENITOR CELLS

(75) Inventor: Noel M. Caplice, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 11/461,709

(22) Filed: Aug. 1, 2006

(65) Prior Publication Data
US 2007/0041953 A1 Feb. 22, 2007

Related U.S. Application Data

(63) Continuation of application No. 10/454,004, filed on Jun. 3, 2003, now abandoned.

(51) Int. Cl.
*C12N 5/08* (2006.01)
(52) U.S. Cl. ..................... 435/372
(58) Field of Classification Search .............. None
See application file for complete search history.

(56) References Cited

U.S. PATENT DOCUMENTS

| 5,130,144 | A | 7/1992 | Civin |
| 5,139,941 | A | 8/1992 | Muzyczka et al. |
| 5,980,887 | A | 11/1999 | Isner et al. |
| 6,913,762 | B2 | 7/2005 | Caplice et al. |
| 7,297,538 | B2 * | 11/2007 | Lee et al. ............ 435/325 |
| 7,387,645 | B2 * | 6/2008 | Fernandes et al. ...... 623/23.75 |
| 2002/0051762 | A1 | 5/2002 | Rafii et al. |
| 2002/0160033 | A1 | 10/2002 | Caplice et al. |
| 2004/0234972 | A1 | 11/2004 | Owens et al. |
| 2004/0247575 | A1 | 12/2004 | Caplice et al. |

FOREIGN PATENT DOCUMENTS

| WO | WO 99/49015 | 9/1999 |
| WO | WO 01/49113 | 7/2001 |
| WO | WO 02/57428 | 7/2002 |

OTHER PUBLICATIONS

Felgner et al., "Enhanced Gene Delivery and Mechanism Studies with a Novel Series of Cationic Lipid Formulations," *J. Biol. Chem.*, 1994, 269:2550-2561.
Kay et al., "Gene therapy," *Proc. Natl. Acad. Sci. USA*, 1997, 94:12744-12746.
Rebar et al., "Induction of angiogenesis in a mouse model using engineered transcription factors," *Nature Medicine*, 2002, 8(12):1427-1432.
Simper et al., "Smooth Muscle Progenitor Cells in Human Blood," *Circulation*, 2002, 106:1199-1204.
Smith et al., "Adenovirus mediated expression of therapeutic plasma levels of human factor IX in mice," *Nat. Genet.*, 1993, 5:397-402.
Spector and Samaniego, "Construction and Isolation of Recombinant Adenoviruses with Gene Replacements," *Meth. Mol. Genet.*, 1995, 7:31-44.
Uchida et al., "HIV, but not murine leukemia virus, vectors mediate high efficiency gene transfer into freshly isolated G0/G1 human hematopoietic stem cells," *Proc. Natl. Acad. Sci. USA*, 1998, 95:11939-11944.
Carmeliet, "Angiogenesis in health and disease," *Nat. Med.*, 2003, 9(6):653-660.
Yeh et al., "Transdifferentiation of Human Peripheral Blood $CD34^+$-Enriched Cell Population Into Cardiomyocytes, Endothelial Cells, and Smooth Muscle Cells In Vivo," *Circulation*, 2003, 108(17):2070-2073.
Zhao et al., "A human peripheral blood monocyte-derived subset acts as pluripotent stem cells," *Proc. Natl. Acad. Sci. USA*, 2003, 100(5):2426-2431.
Hirschi et a l., "PDFG, TGF-β, and Heterotypic Cell—Cell Interactions Mediate Endothelial Cell-induced Recruitment of 10T1/2 Cells and Their Differentiation to a Smooth Muscle Fate," vol. 141(3):805-814 (1998).
Bartunek et al., "Pretreatment of adult bone marrow mesenchymal stem cells with cardiomyogenic growth factors and repair of the chronically infarcted myocardium," *Am J Physiol Heart Circ Physiol.*, 2007, 292:H1095-H1104.
Hoogduijn et al., "Human Heart, Spleen, and Perirenal Fat-Derived Mesenchymal Stem Cells Have Immunomodulatory Capacities," *Stem Cells and Development.*, 2007, 16:597-604.

* cited by examiner

*Primary Examiner*—Michail A Belyavskyi
(74) *Attorney, Agent, or Firm*—Fish & Richardson P.C.

(57) ABSTRACT

Purified populations of smooth muscle progenitor cells are provided as well as methods of making and using the cells.

4 Claims, 7 Drawing Sheets

SMOOTH MUSCLE PROGENITOR CELLS

CROSS-REFERENCE TO RELATED APPLICATIONS

This application is a continuation of and claims priority to U.S. application Ser. No. 10/454,004, filed Jun. 3, 2003.

STATEMENT AS TO FEDERALLY SPONSORED RESEARCH

Funding for the work described herein was provided in part by the federal government: National Institutes of Health grant number HL-66958 P01-NMC. The federal government may have certain rights in the invention.

TECHNICAL FIELD

This invention relates to smooth muscle progenitor cells and methods of using the cells for diagnosing, monitoring, and therapy of vasoproliferative disease.

BACKGROUND

Vascular smooth muscle cell migration, proliferation, and matrix synthesis within the intima of medium-sized and large vessels is thought to play a major role in atherosclerosis development in adult human subjects. In the embryo, these vascular cells have a complex origin, with the first smooth muscle cells surrounding endothelial tubes being derived from trans-differentiated endothelium during nascent vascular and cardiac valve development. Several growth factors have been implicated in embryonic smooth muscle cell differentiation, including transforming growth factors $\beta_1$, $\beta_3$, and platelet-derived growth factor BB (PDGF-BB).

Understanding the phenotype of any circulating smooth muscle progenitor cell may have implications for development of therapies to modulate homing of these cells to the vessel wall. Intrinsic to this latter understanding may be the identification of specific surface adhesion molecules, such as integrins, which are known to be important in homing of blood-borne progenitor cells to specific sites in vivo.

SUMMARY

The invention is based on the identification of smooth muscle progenitor cells (SPCs) in human peripheral blood that can differentiate into smooth muscle like cells, referred to as smooth muscle outgrowth cells (SOCs). In particular, the SPCs differentiate into SOCs in the presence of platelet-derived growth factor (PDGF)-enriched medium. Selection in PDGF-BB-enriched medium caused rapid outgrowth and expansion of SOC to >40 population doublings in a 4-month period. These SOCs were positive for smooth muscle cell-specific α actin (αSMA), myosin heavy chain, and calponin as assayed by immunofluorescence and Western blotting and positive for CD34, Flt1, and Flk1 receptor. The SOCs were negative for Tie-2 receptor expression, indicating a potential bone marrow angioblastic origin. Cells grown in medium alone and the initial mononuclear cell population were negative for these smooth muscle-specific markers.

In one aspect, the invention features an enriched population of adult smooth muscle progenitor cells (e.g., human cells). The cells can be positive for VEGF receptors or CD34, or positive for CD34, Flt1, and Flk receptor, and negative for the Tie-2 receptor, CD31, vWF, and VE-cadherin. In some embodiments, the cells are positive for α-actin, myosin heavy chain, and calponin. The cells can include an exogenous nucleic acid encoding an angiogenic growth factor. The cells can include an exogenous nucleic acid encoding VEGF, fibroblast growth factor-4 (FGF-4), a natiuretic peptide, prostacyclin synthase, nitric oxide synthase, angiostatin, endostatin, erythropoietin (EPO), granulocyte/macrophage colony stimulating factor (GM-CSF), an integrin, or an interleukin.

The invention also features a method for isolating an enriched population of adult smooth muscle progenitor cells. The method includes contacting a mixture of mononuclear cells with platelet-derived growth factor and isolating the population of smooth muscle progenitor cells, wherein the cells are positive for CD34, Flt1, and Flk receptor, and negative for the Tie-2 receptor, CD31, vWF, and VE-cadherin. The contacting step can be performed on a collagen coated substrate. In some embodiments, the cells are cultured in the absence of platelet-derived growth factor.

In another aspect, the invention features a method for obtaining an enriched population of adult smooth muscle progenitor cells. The method includes administering a cytokine (e.g., VEGF, FGF, IGF-I, or SDF) to a subject to recruit multipotent cells to the peripheral blood of the subject; obtaining mononuclear cells from the subject; and contacting the mononuclear cells with platelet-derived growth factor to enrich the population of adult smooth muscle progenitor cells, wherein the cells are positive for CD34, Flt1, and Flk receptor, and negative for the Tie-2 receptor, CD31, vWF, and VE-cadherin. The contacting step can be performed on a collagen-coated substrate.

The invention also features a method for stabilizing vulnerable plaques in a patient. The method includes administering an amount of an enriched population of adult smooth muscle progenitor cells to the patient effective to stabilize vulnerable plaques. The enriched population of adult smooth muscle progenitor cells is autologous to the patient. The cells can include an exogenous nucleic acid encoding an adhesion molecule, wherein the adhesion molecule is expressed on the cell surface. The adhesion molecule can be selected from the group consisting of a selectin, an intracellular adhesion molecule (e.g., ICAM or VCAM), and an extracellular matrix protein such as collagen, fibronectin, laminin, or vitronectin. The population of adult smooth muscle progenitor cells can be pretreated with an extracellular matrix protein before administration to the patient.

In another aspect, the invention features an implantable medical device that includes an enriched population of adult smooth muscle progenitor cells (e.g., human cells). The cells can be positive for CD34, Flt1, and Flk receptor, and negative for Tie-2 receptor, CD31, vWF, and VE-cadherin. The device can be a stent (e.g., a coated stent), a vascular graft, or a hollow tube. The cells can include an exogenous nucleic acid encoding an angiogenic growth factor or an exogenous nucleic acid encoding VEGF, fibroblast growth factor-4 (FGF-4), a natiuretic peptide, prostacyclin synthase, nitric oxide synthase, angiostatin, endostatin, erythropoietin (EPO), granulocyte/macrophage colony stimulating factor (GM-CSF), an integrin, or an interleukin.

In yet another aspect, the invention features a method for monitoring vascular disease in an adult mammal. The method includes determining the number of smooth muscle progenitor cells in the peripheral blood of the adult mammal, and comparing the number of smooth muscle progenitor cells with a baseline number of smooth muscle progenitor cells in a corresponding control population, wherein an altered number of the smooth muscle progenitor cells relative to the baseline number is indicative of a change in the vascular disease. The vascular disease can be atherosclerosis, or can include vulnerable plaque or unstable plaque.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

In FIG. 1A-1B, a single outgrowth colony at week 1 is depicted (A) followed by colony of mixed cell phenotype at week 3 containing polygonal cells (open arrowheads) and spindle-shaped cells (arrows) (B). FIG. 1C depicts confluent SOCs with "hill and valley" morphology. FIG. 1D depicts confluent monolayer of endothelial-like outgrowth cells (EOC) with cobblestone appearance.

DETAILED DESCRIPTION

Figure 1:
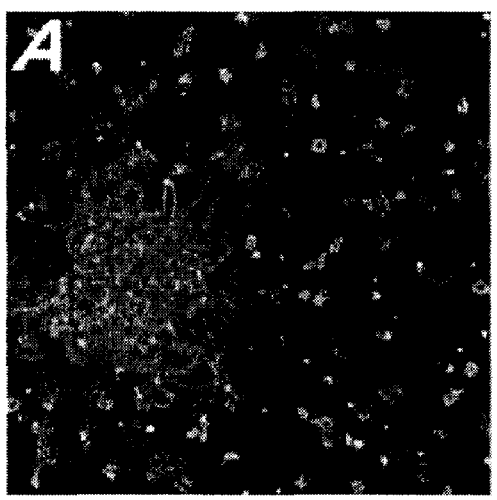
FIG. 1A-1D are photomicrographs obtained after seeding mononuclear cells (MNC) on collagen coated plates and colony formation.
Figure 1:
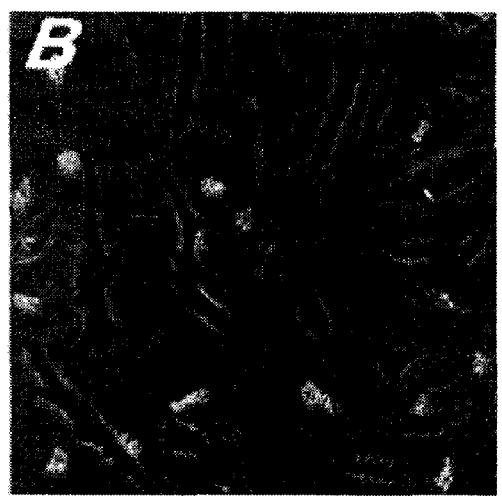
Figure 1:
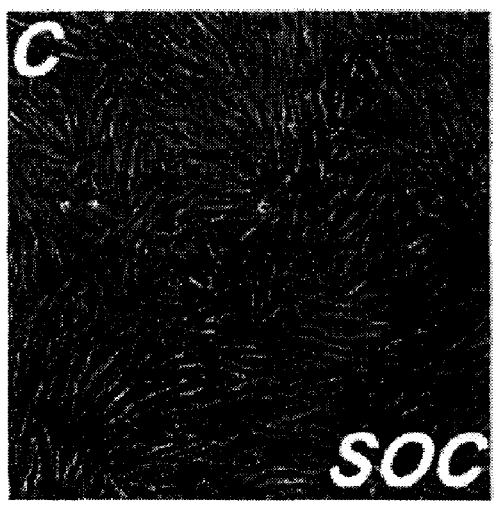
Figure 1:
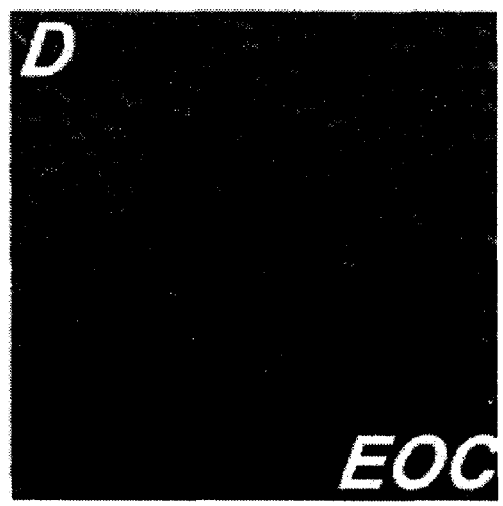

In general, the invention provides purified populations of adult SPCs and methods of using the cells to gain a further understanding of adult vascular smooth muscle cell differentiation, proliferation, and homing, as well as for diagnosis and therapy of vasoproliferative diseases. For instance, these SPCs, or the multipotent cells from which the SPCs originate, can be monitored in blood as a marker for atherosclerosis progression. Ex vivo expansion of these cells may have implications for cell, gene, and tissue engineering approaches to vascular disease. For example, the cells can be manipulated such that adhesion molecules are expressed on the cell surface and used to stabilize vulnerable plaque.

Smooth Muscle Progenitor Cells

As discussed above, the invention provides enriched populations of adult smooth muscle progenitor cells. As used herein, "enriched" means that the population has at least a five fold increase (e.g., at least 10, 15, 20, 25, 50, or 75 fold increase) in SPCs from the crude population of cells from which the SPCs are isolated. As used herein, "smooth muscle progenitor cell" refers to a cell that can develop, either directly or indirectly through one or more intermediate cells, into a smooth muscle cell. SPCs are positive for one or more vascular endothelial growth factor (VEGF) receptors. Examples of VEGF receptors include FLK-1 and FLT-1. The FLK-1 receptor also is known as VEGF receptor-2. Human FLK-1 receptor is known as KDR. SPCs also are positive for CD34, which is characteristic of angioblasts and hematopoietic stem cells. SPCs also are positive for one or more markers of smooth muscle cells, including smooth muscle cell specific α-actin (αSMA), myosin heavy chain, and calponin. The SPCs are further characterized by the absence, or significantly lower expression levels, of certain markers, including the Tie-2 receptor, CD31, vWF, and VE-cadherin. The SPCs also exhibit increased levels of $\alpha_5\beta_1$ expression relative to endothelial progenitor cells.

The SPCs can be isolated from adult mammals, including rodents such as mice and rats, farm animals such as pigs, cattle, sheep, and goats, and humans or other primates. Typically, a mixture of mononuclear cells is obtained from an adult mammal (e.g., from the circulating peripheral blood). In some embodiments, blood can be withdrawn from the circulating peripheral blood of a donor, mononuclear cells can be isolated, and mononuclear cell-depleted blood can be returned to the donor's circulatory system by methods known in the art (e.g., hemapheresis). Alternatively, bone marrow may be obtained from a mammal, such as a human patient undergoing an autologous transplant.

Multipotent cells can be mobilized (i.e., recruited) into the circulating peripheral blood by administering a cytokine to the subject before obtaining mononuclear cells from the subject. Non-limiting examples of cytokines include fibroblast growth factor (FGF), insulin-like growth factor I (IGF-1), stromal cell derived factor (SDF), granulocyte colony stimulating factor (G-CSF), granulocyte macrophage colony stimulating factor (GM-CSF), VEGF, stem cell factor (SCF), or an interleukin (e.g., IL-1 or 8).

Mononuclear cells can be resuspended in endothelial growth medium (EGM-2) and placed in collagen type I coated plates and allowed to grow until cell colonies are formed. The cell colonies can be passaged and cultured on collagen type I coated plates to induce smooth muscle cell differentiation. In some embodiments, the cells are cultured in the presence of PDGF, and in particular PDGF-BB. Typically, smooth muscle cell differentiation is apparent after two weeks of culturing. As described herein, SPCs have an in vitro proliferative potential that is significantly greater than cells that outgrow from EGM-2 in the presence of VEGF.

In some embodiments, the mixture of mononuclear cells can be contacted with an agent that can bind to an antigen on the surface of a SPC (e.g., a VEGF receptor such as FLK-1) or the multipotent cell from which the SPC originates. The binding of the SPCs to the agent permits further enrichment for SPCs by distinguishing SPCs from contaminating cells that do not express the antigen. The agent can be any molecule that has specific binding affinity for an antigen on the surface of a SPC. For example, the agent can be a monoclonal antibody or a fragment thereof, or, in the case of an antigen that is a receptor, the ligand of that receptor. For example, the agent can be an anti-VEGF receptor antibody or an anti-CD34 antibody such as the anti-My-10 monoclonal antibody described in U.S. Pat. No. 5,130,144. The hybridoma cell line that expresses the anti-My monoclonal antibody is available from the American Type Culture Collection, Manassas, Va. The agent can be conjugated with a detectable label such as a fluorophore, which may be used in connection with a fluorescence-activated cell sorter, and the like.

SPCs can be modified such that the cells produce one or more polypeptides or other therapeutic compounds of interest. As used herein, the term "polypeptide" refers to any chain of amino acids, regardless of length or post-translational modification. Typically, modified cells include an exogenous nucleic acid encoding the desired polypeptide (e.g., an angiogenic growth factor). For example, the exogenous nucleic acid can encode an angiogenic growth factor such as VEGF, a fibroblast growth factor such as basic FGF or FGF-4, placental growth factor, hepatocyte growth factor, angiogenin, angiopoietin-1, pleiotrophin, transforming growth factor ($\alpha$ or $\beta$), or tumor necrosis factor $\alpha$. The exogenous nucleic acid also can encode a natiuretic peptide such as an atrial natiuretic peptide (ANP) or a brain natriuretic peptide (BNP), prostacyclin synthase, nitric oxide synthase, angiostatin, endostatin, erythropoietin (EPO), GM-CSF, or an interleukin such as IL-1, 2, 3, 4, 5, 6, 7, 8, 9, 10, 11, 12, 13, 14, 15, 16, 17, or 18. The exogenous nucleic acid also can encode an adhesion molecule such as a selectin (e.g., E, L, or P selectin), an extracellular matrix protein (e.g., collagen type I, III, or IV; fibronectin; laminin; or vitronectin), an integrin (e.g., $\alpha_5\beta_1$), or an intracellular adhesion molecule such as ICAM or a vascular cell adhesion molecule (VCAM).

Therapeutic compounds include small molecules produced by polypeptides (e.g., prostaglandins or nitric oxide (NO)), as well as ribozymes and antisense nucleic acids. As a result, the modified cells can deliver any polypeptide or any therapeutic compound to the mammal for treating any disease, including vascular and renal diseases, hepatic disease, inflammatory diseases such as arthritis, as well as various cancers. In addition, marker polypeptides can be delivered to a patient to aid in diagnostic testing.

To modify the isolated cells such that a polypeptide or other therapeutic compound of interest is produced, the appropriate exogenous nucleic acid must be delivered to the cells. In some embodiments, the cells are transiently transfected, which indicates that the exogenous nucleic acid is episomal (i.e., not integrated into the chromosomal DNA). In other embodiments, the cells are stably transfected, i.e., the exogenous nucleic acid is integrated into the host cell's chromosomal DNA. The term "exogenous" as used herein with reference to a nucleic acid and a particular cell refers to any nucleic acid that does not originate from that particular cell as found in nature. In addition, the term "exogenous" includes a naturally-occurring nucleic acid. For example, a nucleic acid encoding a polypeptide that is isolated from a human cell is an exogenous nucleic acid with respect to a second human cell once that nucleic acid is introduced into the second human cell.

The exogenous nucleic acid can be transferred to the cells using recombinant viruses that can infect cells, or liposomes or other non-viral methods such as electroporation, microinjection, or calcium phosphate precipitation, that are capable of delivering nucleic acids to cells. In either case, the exogenous nucleic acid that is delivered typically is part of a vector in which a regulatory element such as a promoter is operably linked to the nucleic acid of interest. The promoter can be constitutive or inducible. Non-limiting examples of constitutive promoters include cytomegalovirus (CMV) promoter and the Rous sarcoma virus promoter. As used herein, "inducible" refers to both up-regulation and down regulation. An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent such as a protein, metabolite, growth regulator, phenolic compound, or a physiological stress imposed directly by, for example heat, or indirectly through the action of a pathogen or disease agent such as a virus. The inducer also can be an illumination agent such as light and light's various aspects, which include wavelength, intensity, fluorescence, direction, and duration.

An example of an inducible promoter is the tetracycline (tet)-on promoter system, which can be used to regulate transcription of the nucleic acid. In this system, a mutated Tet repressor (TetR) is fused to the activation domain of herpes simplex VP 16 (transactivator protein) to create a tetracycline-controlled transcriptional activator (tTA), which is regulated by tet or doxycycline (dox). In the absence of antibiotic, transcription is minimal, while in the presence of tet or dox, transcription is induced. Alternative inducible systems include the ecdysone or rapamycin systems. Ecdysone is an insect molting hormone whose production is controlled by a heterodimer of the ecdysone receptor and the product of the ultraspiracle gene (USP). Expression is induced by treatment with ecdysone or an analog of ecdysone such as muristerone A.

Additional regulatory elements that may be useful in vectors, include, but are not limited to, polyadenylation sequences, translation control sequences (e.g., an internal ribosome entry segment, IRES), enhancers, or introns. Such elements may not be necessary, although they may increase expression by affecting transcription, stability of the mRNA, translational efficiency, or the like. Such elements can be included in a nucleic acid construct as desired to obtain optimal expression of the nucleic acids in the cell(s). Sufficient expression, however, may sometimes be obtained without such additional elements.

Vectors also can include other elements. For example, a vector can include a nucleic acid that encodes a signal peptide such that the encoded polypeptide is directed to a particular cellular location (e.g., the cell surface) or a nucleic acid that encodes a selectable marker. Non-limiting examples of selectable markers include puromycin, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture.

Viral vectors that can be used include adenovirus, adeno-associated virus (AAV), retroviruses, lentiviruses, vaccinia virus, measles viruses, herpes viruses, and bovine papilloma virus vectors. See, Kay et al. (1997) *Proc. Natl. Acad. Sci. USA* 94:12744-12746 for a review of viral and non-viral vectors. Viral vectors are modified so the native tropism and pathogenicity of the virus has been altered or removed. The genome of a virus also can be modified to increase its infectivity and to accommodate packaging of the nucleic acid encoding the polypeptide of interest.

Adenoviral vectors can be easily manipulated in the laboratory, can efficiently transduce dividing and nondividing cells, and rarely integrate into the host genome. Smith et al. (1993) *Nat. Genet.* 5:397-402; and Spector and Samaniego (1995) *Meth. Mol. Genet.*, 7:31-44. The adenovirus can be modified such that the E1 region is removed from the double stranded DNA genome to provide space for the nucleic acid encoding the polypeptide and to remove the transactivating E1a protein such that the virus cannot replicate. Adenoviruses have been used to transduce a variety of cell types, including, inter alia, keratinocytes, hepatocytes, and epithelial cells.

Adeno-associated viral (AAV) vectors demonstrate a broad range of tropism and infectivity, although they exhibit no human pathogenicity and do not elicit an inflammatory response. AAV vectors exhibit site-specific integration and can infect non-dividing cells. AAV vectors have been used to deliver nucleic acid to brain, skeletal muscle, and liver over a long period of time (e.g., >9 months in mice) in animals. See, for example, U.S. Pat. No. 5,139,941 for a description of AAV vectors.

Retroviruses are the most-characterized viral delivery system and have been used in clinical trials. Retroviral vectors mediate high nucleic acid transfer efficiency and expression. Retroviruses enter a cell by direct fusion to the plasma membrane and integrate into the host chromosome during cell division.

Lentiviruses also can be used to deliver nucleic acids to cells, and in particular, to non-dividing cells. Replication deficient HIV type I based vectors have been used to transduce a variety of cell types, including stem cells. See, Uchidda et al. (1998) *Proc. Natl. Acad. Sci. USA* 95:11939-11944.

Non-viral vectors can be delivered to cells via liposomes, which are artificial membrane vesicles. The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Transduction efficiency of liposomes can be increased by using dioleoylphosphatidylethanolamine during transduction. See, Felgner et al. (1994) *J. Biol. Chem.* 269:2550-2561. High efficiency liposomes are commercially available. See, for example, SuperFect® from Qiagen (Valencia, Calif.).

Methods for Using SPCs

SPCs can be used to examine adult vascular smooth muscle cell differentiation, proliferation, and homing, as well as for diagnosis and therapy of vasoproliferative diseases. For example, SPCs, or the multipotent cells from which the SPCs originate, can be monitored in blood as a marker for vascular disease in adult mammals (e.g., human patients). For example, the method can be used to monitor vulnerable plaques, unstable plaques, or atherosclerosis progression in adult mammals. The number of SPCs can be determined in an adult mammal using known cytological methods and compared to a baseline number of SPCs in a corresponding control population. An alteration in the number of SPCs in the patient from baseline is indicative of a change in the disease (e.g., atherosclerosis progression). The control population can be patients with no or minimal disease. Alternatively, the baseline can be the number of SPCs in a given patient before treatment is initiated. As the patient undergoes therapy, the number of SPCs can be monitored in the patient and compared with the baseline to determine if the treatment is of clinical benefit to the patient. SPCs also can be used in patients with pressure sores to encourage wound healing or scar formation.

Ex vivo expansion of these cells may have implications for cell, gene, and tissue engineering approaches to vascular disease. For example, the cells can be used to stabilize vulnerable plaque in a patient by administering an amount of a purified population of SPCs to the patient effective to stabilize vulnerable plaques. In some embodiments, the SPCs can be manipulated such that adhesion molecules are expressed on the cell surface. As discussed above, the SPCs can be engineered such that the SPCs include an exogenous nucleic acid encoding an adhesion molecule (e.g., an integrin). Alternatively, the SPCs can be treated in vitro by priming the SPCs to attach to a particular extracellular matrix. For example, an extracellular matrix from a patient (e.g., material from an arteriosclerotic plaque, which can be obtained from an atherectomy) can be coated on a tissue culture plate and the SPCs primed to attach to the particular matrix. SPCs that attach are expanded then injected into the patient, where the cells will target plaques having similar extracellular matrices.

In other embodiments, an implantable medical device (e.g., a stent, including a coated stent, graft such as a vascular graft, sheet, hollow tube, or valve) can include SPCs. For example, the SPCs can be seeded onto a device. See, for example, U.S. Patent Publication No. US-2002-0160033-A1. For example, SPCs can be used to form living vascular grafts, including arterial, venous, and renal grafts or living prosthetic valves for venous and cardiac applications. SPCs also can be used to create implantable sphincters, to aid in spinal cord regeneration, reline the aorta in patients with shaggy aorta, or repair irreversibly damaged myocardium. To further enhance such repairs, SPCs can be combined with endothelial progenitor cells.

To treat cardiovascular disease, cells can be engineered to produce cell mitogens such as VEGF or FGF-4, ANP, and combinations of such polypeptides and seeded onto a medical device, which then is implanted in a patient. In particular, a stent containing cells that secrete VEGF can be used to treat patients with peripheral vascular disease, distal coronary disease, or chronic total occlusions unsuitable for conventional revascularization approaches. Expression of prostacyclin synthase, which produces prostacyclin ($PGI_2$) from prostaglandin $H_2$ ($PGH_2$), in cells can result in delivery of $PGI_2$ to tissues and can be used for relaxing vascular smooth muscle. Expression of nitric oxide synthase, which catalyzes the production of NO, in cells can result in delivery of NO to tissues and can be used, for example, to inhibit restenosis. Antiangiogenic polypeptides such as angiostatin and endostatin can be used to aid in the treatment of angiogenic dependent tumors and micrometastases in patients. A similar strategy can be used to aid treatment of biliary duct tumors. Hematopoietic growth factors such as EPO, GM-CSF, and interleukins can be used to increase production of blood cells. For example, EPO can be used to stimulate red cell production and to treat anemia.

In other embodiments, the SPCs are used to identify compounds that may be useful as anti-restenosis agents. SPCs are particularly useful for drug screening due to ease in which the cells can be obtained. Drug screening assays can be performed by contacting the SPCs with a test compound and determining if proliferation of the SPCs is inhibited. A "test compound" can be a biological macromolecule such as an oligonucleotide or a peptide, a chemical compound, a mixture of chemical compounds (e.g., from a combinatorial library), or an extract isolated from bacterial, plant, fungal, or animal matter.

The invention will be further described in the following examples, which do not limit the scope of the invention described in the claims.

EXAMPLES

Methods and Materials

Study Subjects

Six blood samples were used from five healthy human volunteer donors (three male and two female, age 26 to 38 years) according to a protocol previously approved by the institutional review board. Fresh blood was collected by venipuncture and anticoagulated in citrate phosphate dextrose solution (Baxter).

Buffy Coat Preparation and Vascular Progenitor Cell Culture

Human mononuclear cells (MNCs) were initially isolated from peripheral buffy coat blood in Histopaque-1077 followed by washing in MCDB 131 supplemented with hydrocortisone, antibiotics, and 10 ng/mL VEGF. Mononuclear cells were then resuspended in EGM-2 medium and placed on 3 wells of a 6-well plate coated with collagen type I (Becton Dickinson). At 4 weeks, subconfluent cell colonies were passaged and cells were subsequently cultured in either EGM-2 to maintain endothelial cell phenotype or EGM-2 supplemented with PDGF BB (50 ng/mL, R&D Systems) to facilitate smooth muscle cell differentiation. Human vascular smooth muscle cells (hVSMCs) were obtained from Clonetics, and human fibroblasts (hFBs) were obtained from ATCC. In separate experiments, CD34+ve mononuclear cells (90% purity) were selected using immunomagnetic beads and the MACS technique (Miltenyi Biotech), and these cells were similarly differentiated on collagen type I matrix, as described above.

Evaluation of Smooth Muscle Outgrowth Cell Phenotype

Morphological appearance and indirect immunofluorescence were used to define smooth muscle cell phenotype. Primary antibodies were used against CD34 (Immunotech IM 1869), α smooth muscle actin (ASMA), smooth muscle myosin heavy chain (MHC), and calponin (all from Dako Corp). In each immunofluorescence experiment, an isotype-matched IgG control was also used. Binding of primary antibodies to progenitor cells was detected with Alexa-Fluor 488-conjugated anti-mouse IgG (Eugene, Oreg.). Antibodies to human vWF (Dako Corp, Carpenteria, Calif.), VE-Cadherin (Santa Cruz Biotechnology, Santa Cruz, Calif.), and CD31 (Sigma Co, St Louis, Mo.) were used to label EOC, as previously described. These markers allowed definition of cells as smooth muscle or endothelial lineage.

Western Blot Analysis

Western blotting was performed to identify vascular smooth muscle cell-specific cytoskeletal protein, VEGF receptor, and Tie-2 receptor expression in SOCs. Briefly, cells were homogenized in lysis buffer containing 50 mmol/L Tris HCl (pH 8.0), 150 mmol/L NaCl, 0.02% sodium azide, 0.1% SDS, 100 µg/mL PMSF, and 1 µg/mL aprotinin. The lysate had protein content determined by Bradford assay, and equal amounts of protein were denatured by boiling, reduced in 1 mmol/L DTT, followed by electrophoresis in 12% SDS-polyacrylamide gel. The protein was transferred to nitrocellulose and immunoblotted using monoclonal antibodies to aSMA, human smooth muscle MHC, human calponin, and Flk1 (Santa Cruz Biotechnology) and polyclonal antibodies to Flt1 (R&D Systems, Minneapolis, Minn.) and Tie-2 receptor (Santa Cruz Biotechnology, Santa Cruz, Calif.) at dilutions of 1:500. Secondary anti-mouse, anti-rabbit, and anti-goat antibodies conjugated to horseradish peroxidase (Calbiochem, San Diego, Calif.) at a 1:1000 dilution were used for detection using chemoluminescence (Supersignal, Pierce) and x-ray film exposure (Kodak). hVSMCs and hFBs were used as positive and negative control cells for smooth muscle-specific markers.

FACS Analysis

FACS was performed to identify both cell-surface and intracellular antigens in MNC, SOC, and EOC. Primary antibodies to ASMA, CD31, and integrin $\alpha_5\beta_1$ were used with secondary detection using an FITC-conjugated antibody in each case. Isotype-matched IgG antibodies were used as a control, and the fluorescent intensity of stained cells was gated according to established methods.

Outgrowth Cell Integrin $\alpha_5\beta_1$ Expression and Adhesion Assay

Integrin $\alpha_5\beta_1$ expression on MNC, EOC, and SOC was quantitated using FACS analysis. Integrin $\alpha_5\beta_1$ in EOC and SOC was also analyzed by Western blotting using cell lysates electrophoresed on a 4% to 20% gradient SDS-PAGE. Equal amounts of protein were transferred to nitrocellulose, and α and β subunits were immunodetected using a primary antibody to the human integrin $\alpha_5\beta_1$ (10 µg/mL, Chemicon, Temecula, Calif.) and a secondary anti-mouse HRP conjugate (1:500), as described above. Equal loading of protein was confirmed by use of α-tubulin antibody.

To confirm the adhesive function of surface $\alpha_5\beta_1$ integrin expression on each outgrowth cell type, adhesion assays on human fibronectin (10 µg/mL, Sigma) were performed. Both EOC and SOC at a density of 1.5×10 cells/well on a 6-well culture plate were allowed to adhere in basal medium (EBM-2) with 0.1% BSA in the presence or absence of a primary antibody to human integrin $\alpha_5\beta_1$ (10 µg/mL) or a mouse IgG control antibody at a similar concentration. Nonadherent cells were then washed off, and adherent cells were lifted with trypsin and subsequently counted with a hemocytometer. Percentage adhesion was calculated by dividing the number of adherent cells by the total number of cells plated per well.

Outgrowth Cell Proliferation Assay

Both SOC and EOC at a similar passage were seeded at a density of 5×10 per well on a 24-well plate coated with collagen type I and incubated overnight with EGM-2 and 5% FCS. Similar initial seeding density was confirmed 12 hours after plating by use of a cell-titer MTS assay (Cell-Titer AQ, No. G5421, Promega). This generated a baseline seeding absorbance for both cell types. All cells were then growth arrested for 24 hours in serum-free EBM-2. Cells were released from growth arrest with addition of EGM-2 and 5% FCS, and the cell number in each well was determined by cell titer assay at 2, 4, 6, and 8 days after serum stimulation. The absorbance generated at each time point was expressed as a ratio of the initial seeding absorbance obtained for each progenitor cell type.

Statistics

All data are presented as mean±SEM. Comparison between groups was made using one-way ANOVA. $P<0.05$ was considered statistically significant.

Example 1

Vascular Progenitor Response to Growth Factor Selection

Approximately 6 to 8 colonies per initial patient MNC sample seeded on collagen type I matrix with EGM-2 culture medium (FIG. 1A) grew out over a 3-week period, at which time a mixed population existed of polygonal- and stellate shaped cells (FIG. 1B). These mixed cultures were passaged and split into 2 plates, which were subsequently grown in either EGM-2 with high levels of PDGF BB or EGM-2 alone to encourage smooth muscle cell and endothelial cell growth, respectively. The cells maintained in the PDGF BB-enriched medium became predominantly smooth muscle-appearing cells with a "hill and valley morphology" (FIG. 1C) within an additional 2-week period. These SOCs grew at a rapid rate, achieving >40 population doublings over a 4-month period from the time of initial colony formation. The endothelial outgrowth cells (EOCS) exhibited a typical cobblestone morphology (FIG. 1D) and grew at a slower rate, achieving ≈20 population doublings in the 4 months after colony formation. Similar differentiation was seen when using an initial CD34+ve mononuclear population to derive outgrowth cells.

Example 2

Immunophenotyping of Smooth Muscle Outgrowth Cells

Figure 2:
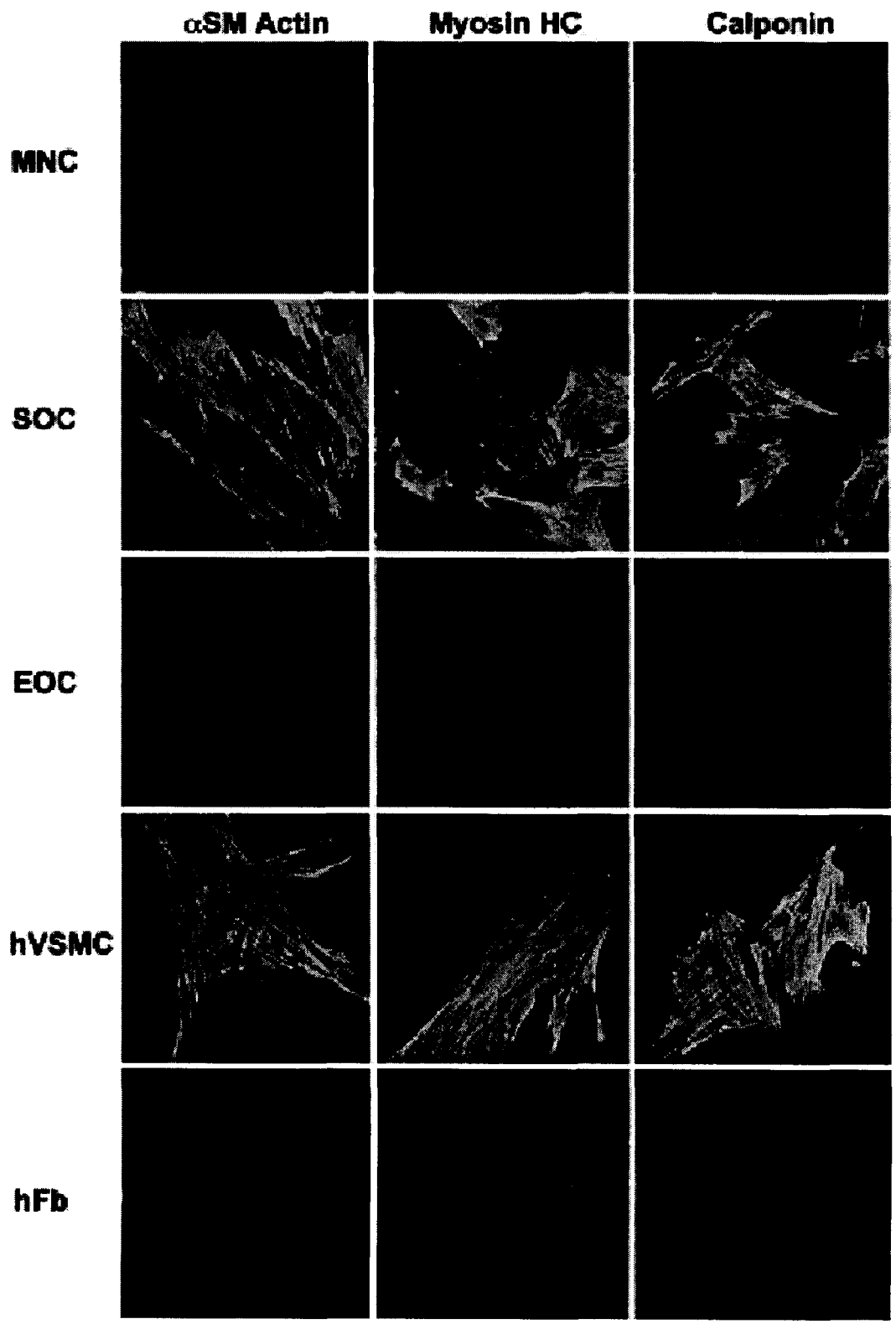
FIG. 2 contains photographs of the immunofluorescence of MNC, SOC, and EOC labeled with antibodies to αSMA, smooth muscle MHC, and calponin. The secondary antibodies in each case were conjugated to Alexa-fluor. Cell nuclei were counterstained with Hoechst stain (blue). hVSMCs were used as a positive control and hFbs as a negative control for the SMC-specific markers.
Figure 3:
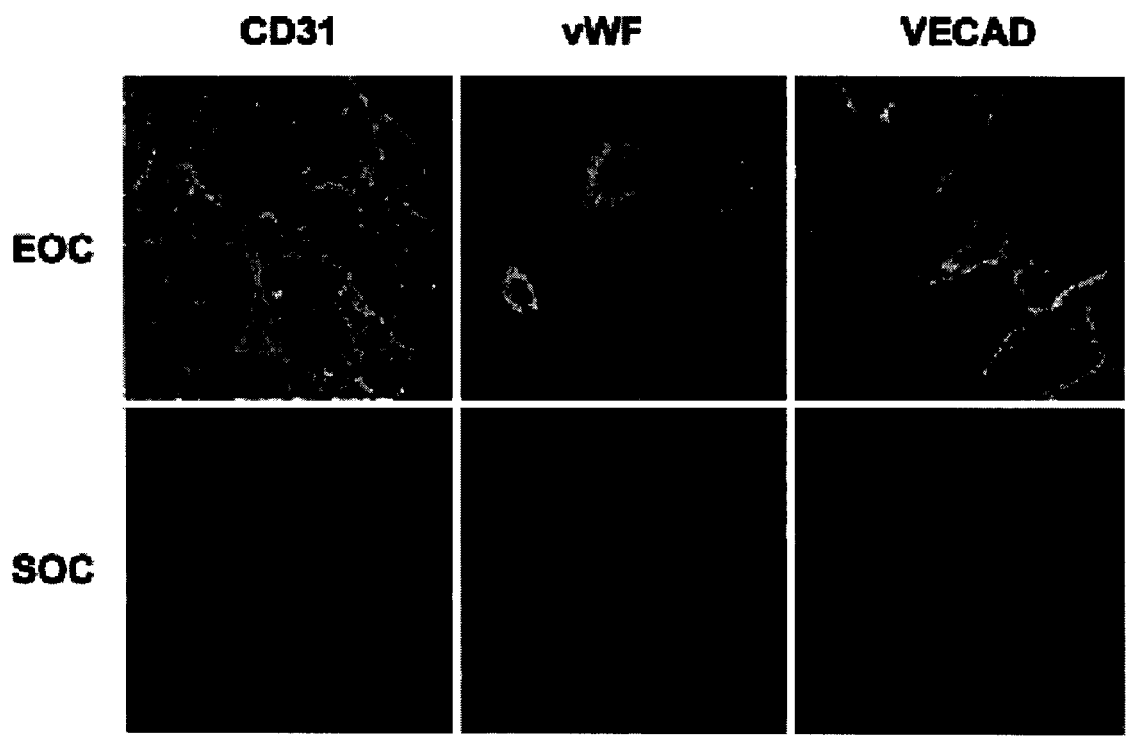
FIG. 3 contains photographs of the immunofluorescence of EOC and SOC labeled with antibodies to CD31, vWF, and VE cadherin. The secondary antibodies in each case were conjugated to Alexa-fluor. Cell nuclei were counterstained with Hoechst stain.
Figure 4:
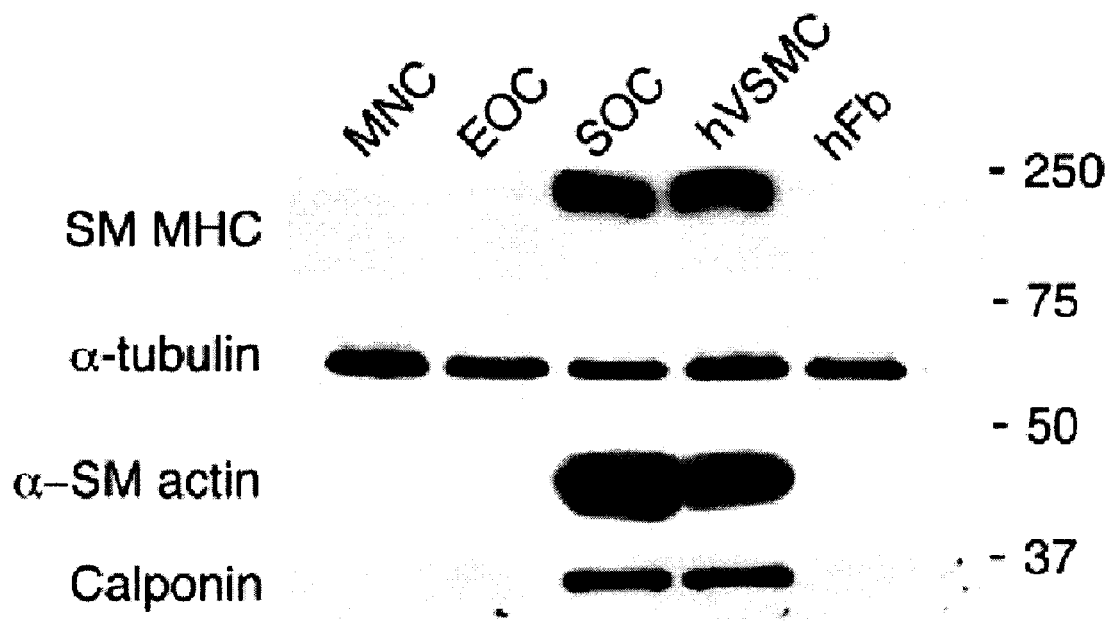
FIG. 4 is a Western blot of smooth muscle cell-specific proteins from MNC, EOC, and SOC lysates run on SDS-PAGE. SOC lysates were immunoreactive for αSMA, smooth muscle MHC, and calponin at appropriate molecular weights, whereas EOC and the initial MNC population were nonimmunoreactive for all smooth muscle-specific antibodies. A positive control lysate (hVSMC) and a negative control lysate (hFb) were used to determine specificity of the antibodies. The loading control used was α-tubulin.

To additionally evaluate phenotype, cells were stained using smooth muscle cell-specific antibodies. Subconfluent SOC stained positive for αSMA, smooth muscle MHC, and calponin (FIG. 2) on indirect immunofluorescence, whereas the starting MNC population and EOC stained negatively for all smooth muscle cell markers (FIG. 2). Similarly, hVSMCs in culture stained positively, whereas hFBs stained negatively for all smooth muscle-specific markers (FIG. 2). EOCs were confirmed positive for endothelial markers such as CD31, vWF, and VECadherin, whereas SOC stained universally negative for all endothelial markers (FIG. 3). In each case, the isotype matched IgG control antibody stained negatively. To confirm the presence of smooth muscle-specific proteins in SOC but not in MNC or EOC, cell lysates from each cell type were run on SDS-PAGE, immunoblotted, and confirmed to have αSMA, smooth muscle MHC, and calponin protein at appropriate molecular weights (FIG. 4). Positive hVSMC and negative hFB controls also showed appropriate presence and absence of immunoreactivity for smooth muscle-specific markers (FIG. 4).

Figure 5:
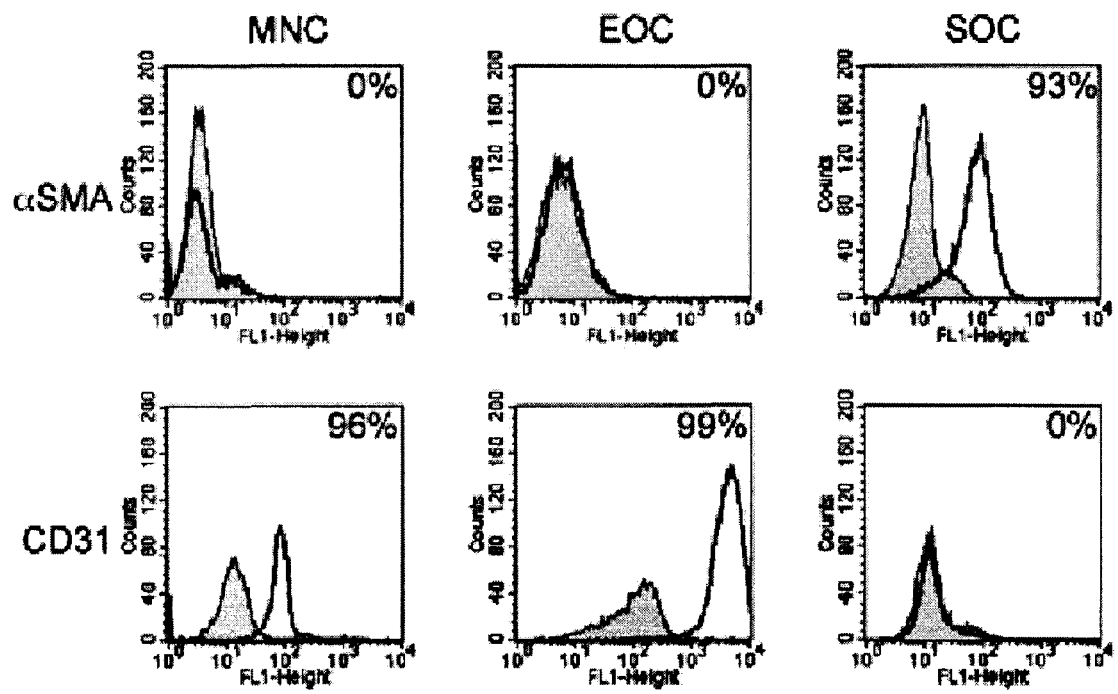
FIG. 5 is a FACS analysis of intracellular αSMA and cell-surface CD31 in MNC, EOC, and SOC. The open heavy-lined histograms represent the test antibodies (anti-αSMA and anti-CD31) and the filled histograms represent the iso-type-matched control IgG antibodies.

To quantify the intensity of staining and the percentage of positive cells expressing αSMA and CD31 in each population (MNC, SOC, and EOC), intracellular (αSMA) and cell surface (CD31) antigens were determined by FACS. The smooth muscle-specific marker (αSMA) was detected in 0% of both MNC and EOC populations, whereas 93% of SOC were positive for this marker at high intensity (FIG. 5). Similarly, CD31 was detected in 0% of SOC but in 96% and 99% of MNC and EOC, with a much higher intensity of CD31 staining in the EOC compared with the MNC population (FIG. 5).

Figure 6:
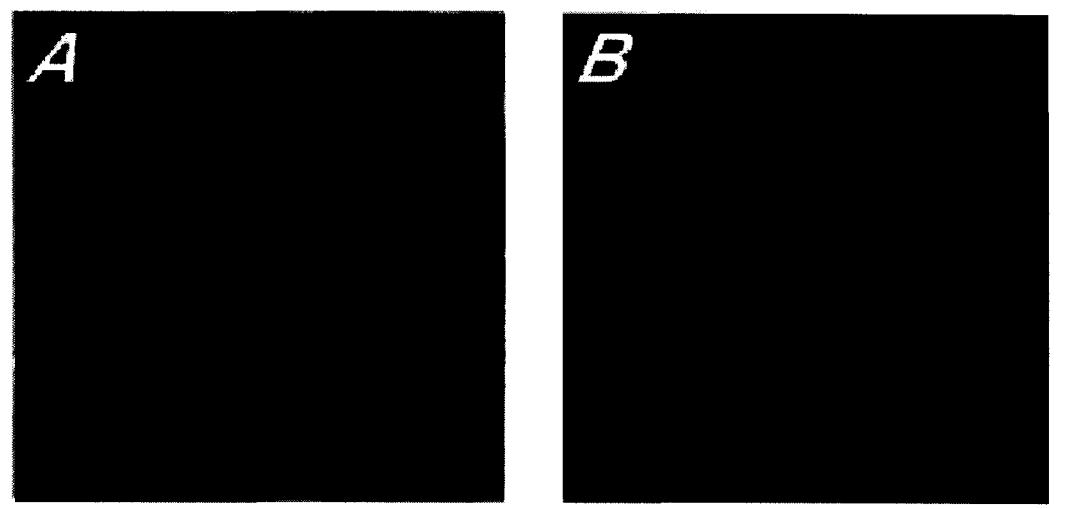
FIGS. 6A and 6B are photographs of the immunofluorescence of SOC labeled with a primary CD34 antibody and secondary Cy3 conjugated antibody showing punctate surface CD34 labeling (6A) and an isotype-matched control IgG antibody stained negatively (6B).
FIG. 6C contains three immunoblots of SOC and EOC lysates showing presence of Flt-1 and Flk-1 VEGF receptors in each outgrowth cell. In the case of Tie-2 receptor, EOC but not SOC lysates were positively immunoreactive. α-tubulin was used as a loading control in each case.
Figure 6:
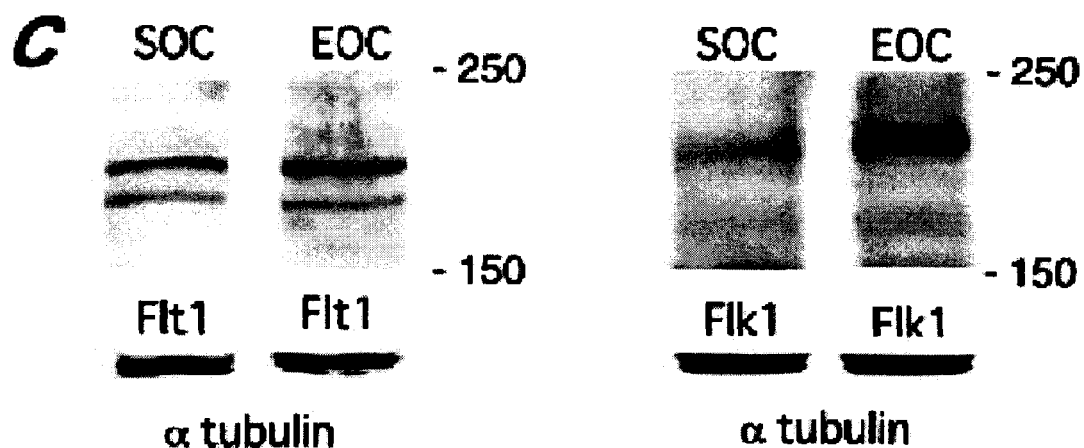
Figure 6:
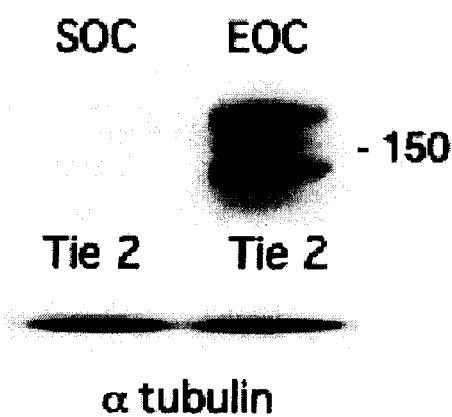

Hematopoietic origin of SOC was confirmed by positive immunofluorescence staining for CD34 (FIGS. 6A and 6B). Furthermore, SOC lysates showed significant levels of both VEGF receptors (Flt1 and Flk1) (FIG. 6C) on Western blotting, consistent with what has previously been described for endothelial outgrowth cells, whereas SOC lysates were negatively immunoreactive for the Tie-2 receptor compared with EOC (FIG. 6C).

Example 3

Integrin $\alpha_5\beta_1$ Expression, Matrix Adhesion, and Cell Proliferation

Figure 7:
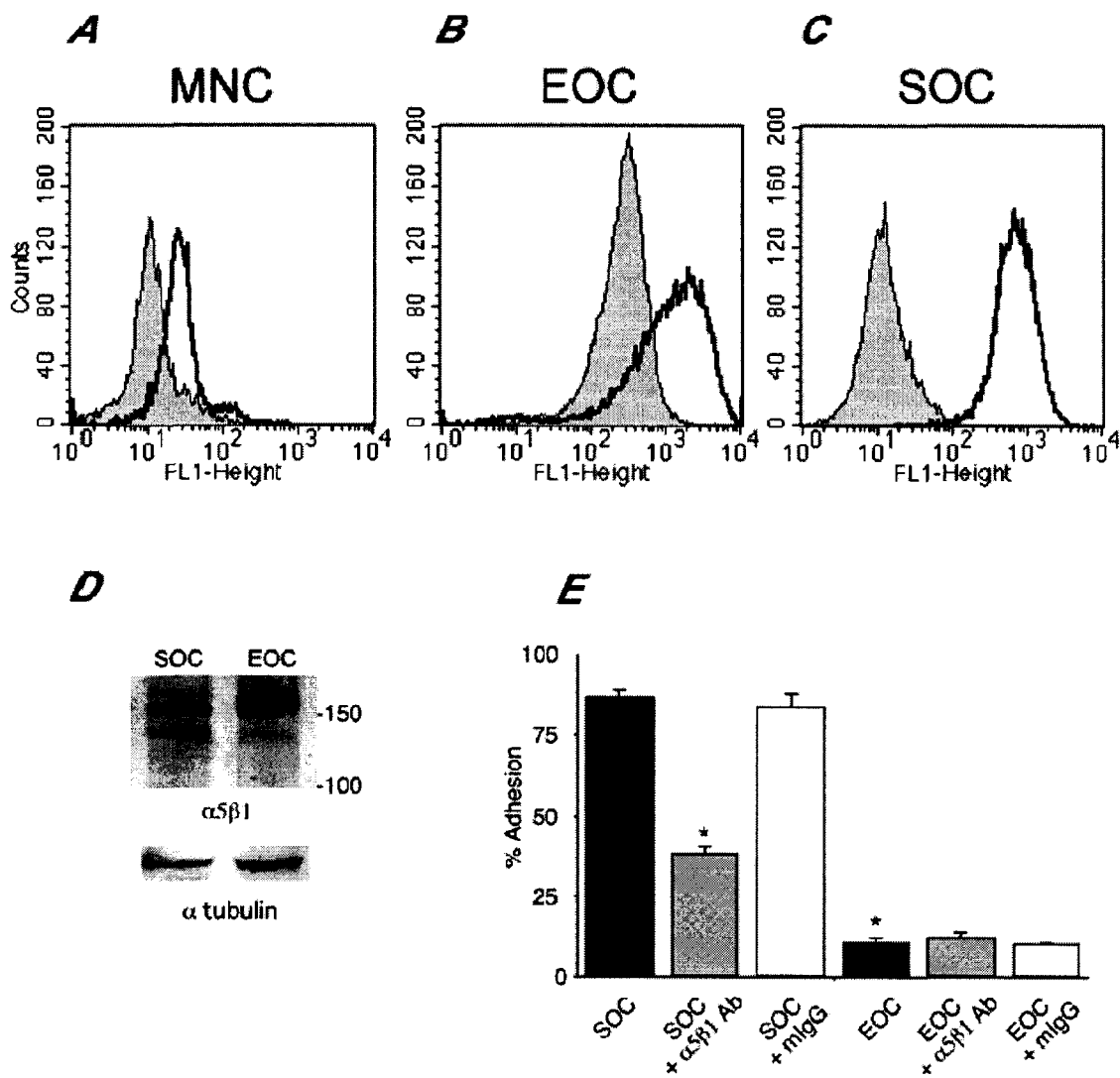
FIG. 7A-7C are FACS analysis of surface expression of integrin $\alpha5\beta1$ on MNC (A), EOC (B), and SOC (C).
FIG. 7D is a Western blot analysis of SOC and EOC membrane lysates showing very positive immunoreactivity for integrin $\alpha5\beta1$ subunits in SOC compared with EOC.
FIG. 7E is a graph of the adhesion of cultured human SOC and EOC to human fibronectin in the presence and absence of an antibody to $\alpha5\beta1$ integrin and mouse IgG control (mIgG). *P<0.001 compared with SOC alone (n=4 for all experiments).
Figure 8:
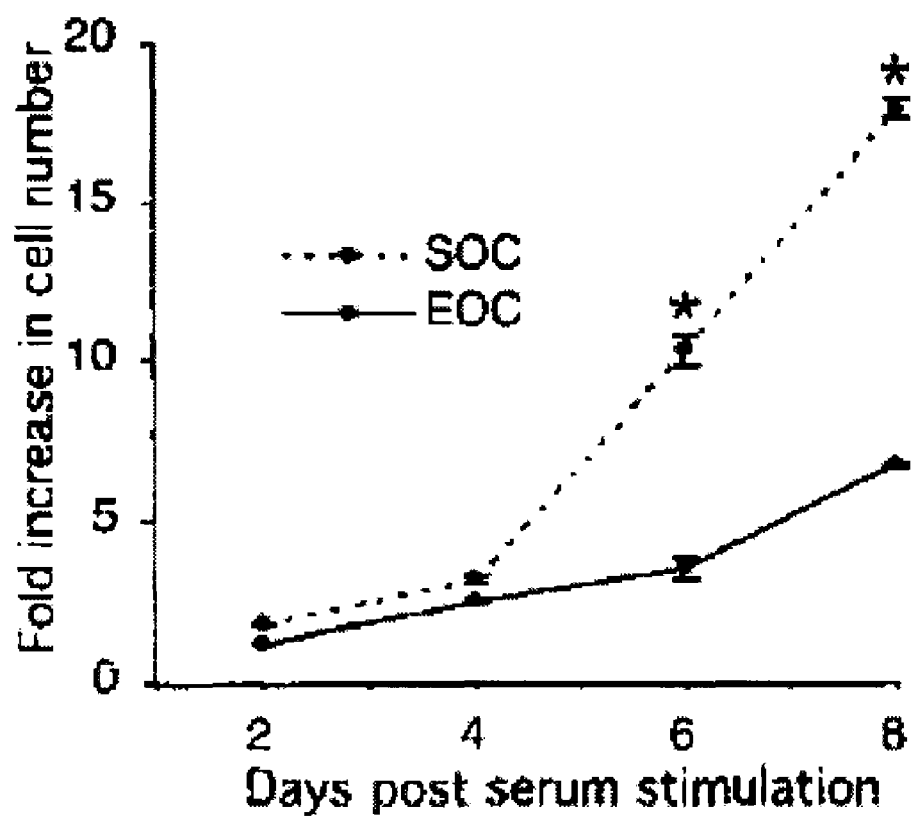
FIG. 8 is a graph depicting cell proliferation of similar passage SOC and EOC after release from growth arrest with 5% FCS. *P<0.001 compared with EOC at the same time period after growth arrest (n=3 for all experiments).

Cell-surface integrin $\alpha_5\beta_1$ expression on MNC, EOC, and SOC was quantitated by FACS. SOC showed increased $\alpha_5\beta_1$ intensity and increased numbers of cells staining positive for this integrin compared with EOC and MNC (FIG. 7). These data were confirmed by Western blotting of cell lysates, with SOC showing much higher levels of $\alpha_5$ and $\beta_1$ integrin subunit proteins compared with EOC (FIG. 7). To test the functional significance of increased integrin $\alpha_5\beta_1$ expression on SOC compared with EOC, a fibronectin adhesion assay was performed. SOC showed an 8-fold greater adherence to fibronectin compared with EOC ($P<0.001$), and this effect could be significantly inhibited ($P<0.01$) using an $\alpha_5\beta_1$ antibody, whereas similar concentrations of isotype-matched mouse IgG had no such effect (FIG. 7). Moreover, SOC, when released from growth arrest with serum, had a significantly (4- to 5-fold, $P<0.001$) increased rate of proliferation compared with EOC of similar passage and seeding density (FIG. 8).

In summary, several lines of evidence are presented to demonstrate that hematopoietic mononuclear cells do indeed differentiate in culture into smooth muscle cells. First, smooth muscle outgrowth cells (SOC) grown out from mononuclear cells show classic smooth muscle morphology and immunophenotype, but were CD34 positive, a surface marker known to be absent from adult human smooth muscle cells. Second, no smooth muscle cell-specific markers were detected in freshly isolated mononuclear cells either by FACS, Western blotting, or immunofluorescence staining. Third, mononuclear cells cultured in the presence of VEGF rather than PDGF expanded into endothelial monolayers that were negative for smooth muscle cell-specific markers by FACS, Western blotting, and immunofluorescence. Fourth, expanded SOC showed a capacity for extended growth in culture (>40 population doublings) in contrast to adult human smooth muscle cells, which become senescent after 40 population doublings. Together, these data make it extremely unlikely that the SOC observed in this study resulted from contaminating adult smooth muscle cells.

PDGF BB promoted adult smooth muscle cell differentiation and expansion from progenitor colonies of mixed morphological appearance in this study, whereas VEGF did not. It has previously been shown that PDGF BB is implicated in embryonic smooth muscle cell differentiation, and the present study would support a potential role for PDGF BB in differentiation of smooth muscle cells from putative progenitors in circulating blood. Indeed, whereas PDGF BB expression is tightly regulated in vivo, it is known to be released from platelets and is upregulated at sites of endothelial perturbation and vascular injury. Because these sites of PDGF BB expression are precisely where vascular smooth muscle cell proliferation occurs, it is possible to speculate that interaction between PDGF BB and circulating SPC could occur at the blood-vessel wall interface.

SOCs in this study expressed both VEGF 1 and 2 receptors but not Tie-2 receptor, consistent with an angioblastic lineage distinct from EOC that has previously been described as Tie-2 receptor positive. This nonendothelial phenotype of SOC is supported by a morphological and protein expression phenotype of these cells, which was different from EOCs grown from the same MNC pool, and by a lack of CD31, VE cadherin, vWF, and Tie-2 receptor labeling in these cells.

Integrin $\alpha_5\beta_1$ expression and adhesion to fibronectin were markedly increased in SOC compared with EOC in this study, the latter functional effect being significantly inhibited by $\alpha_5\beta_1$ integrin antibody. Finally, SOC showed a significantly greater in vitro proliferative potential compared with EOCs of similar passage ($P<0.001$).

Conclusions. These data suggest that SOC rather than EOC might preferentially attach to fibronectin extracellular matrix. This integrin profile could potentially allow differentiated circulating SPC to attach to sites in vivo, where fibronectin or other $\alpha_5\beta_1$ adhesive matrices, such as fibrin, are exposed to flowing blood. Because these conditions frequently exist after endothelial perturbation or plaque rupture, it is possible that fibrin clot or exposed subendothelial fibronectin in the vessel wall could serve as the soil in which circulating SPCs attach and proliferate. The proliferative capacity of SOC is supported by much higher rates of in vitro cell growth seen in SOC compared with EOC in this study. Together, these data support a paradigm for circulating SPC with the potential for differentiation, homing, and proliferation at sites rich in extracellular matrix proteins such as fibronectin.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An enriched population of blood-derived, adult smooth muscle progenitor cells, wherein said cells are isolated human cells, are positive for CD34, and lack exogenous nucleic acid.

2. The enriched population of adult smooth muscle progenitor cells of claim 1, wherein said cells are positive for VEGF receptors.

3. The enriched population of adult smooth muscle progenitor cells of claim 2, wherein said cells are positive for Flt1 and Flk receptor, and negative for the Tie-2 receptor, CD31, vWF, and VE-cadherin.

4. The enriched population of adult smooth muscle progenitor cells of claim 1, wherein said cells are positive for a-actin, myosin heavy chain, and calponin.

* * * * *

UNITED STATES PATENT AND TRADEMARK OFFICE
CERTIFICATE OF CORRECTION

| | | |
|---|---|---|
| PATENT NO. | : 7,790,453 B2 | Page 1 of 1 |
| APPLICATION NO. | : 11/461709 | |
| DATED | : September 7, 2010 | |
| INVENTOR(S) | : Noel M. Caplice | |

It is certified that error appears in the above-identified patent and that said Letters Patent is hereby corrected as shown below:

Column 14, line 29 (Claim 4), please delete "a-actin" and insert --α-actin-- therefor.

Signed and Sealed this
Second Day of August, 2011

David J. Kappos
*Director of the United States Patent and Trademark Office*